(12) United States Patent
Starr et al.

(10) Patent No.: US 7,857,768 B2
(45) Date of Patent: Dec. 28, 2010

(54) INTEGRATED TAIL MOUNTED BLOOD PRESSURE MONITOR AND PULSE OXIMETER SYSTEM FOR ANIMAL RESEARCH

(75) Inventors: Eric W Starr, Allison Park, PA (US); Bernard F. Hete, Kittanning, PA (US); Eric J Ayers, Alliquippa, PA (US)

(73) Assignee: Starr Life Sciences Corporation, Oakmont, PA (US)

( * ) Notice: Subject to any disclaimer, the term of this patent is extended or adjusted under 35 U.S.C. 154(b) by 80 days.

(21) Appl. No.: 12/249,044

(22) Filed: Oct. 10, 2008

(65) Prior Publication Data

US 2009/0099425 A1 Apr. 16, 2009

Related U.S. Application Data

(60) Provisional application No. 60/978,813, filed on Oct. 10, 2007.

(51) Int. Cl.
*A61B 5/0205* (2006.01)
*A61B 5/1455* (2006.01)
*A61B 5/022* (2006.01)

(52) U.S. Cl. .................. 600/483; 600/323; 600/485

(58) Field of Classification Search ......... 600/322–324, 600/481, 484, 485, 500, 529, 483
See application file for complete search history.

(56) References Cited

U.S. PATENT DOCUMENTS

| | | | |
|---|---|---|---|
| 2,706,927 A | 4/1955 | Wood | |
| 3,094,101 A | 6/1963 | Porter | |
| 3,167,658 A | 1/1965 | Richter | |
| 3,599,629 A | 8/1971 | Gordy | |
| 3,602,213 A | 8/1971 | Howell et al. | |
| 3,625,185 A | 12/1971 | Kester | |
| 3,638,640 A | 2/1972 | Shaw | |
| 3,704,706 A | 12/1972 | Herezfeld et al. | |
| 3,720,199 A | 3/1973 | Richton et al. | |
| 3,769,974 A | 11/1973 | Smart et al. | |
| 3,807,388 A | 4/1974 | Om et al. | |
| 3,819,276 A | 6/1974 | Kiess et al. | |

(Continued)

OTHER PUBLICATIONS

Design of Pulse Oximeters, in the Institute of Physics Publishing, Bristol Philadelphia, 1997, Edited by J.G. Webster.

(Continued)

*Primary Examiner*—Charles A Marmor, II
*Assistant Examiner*—Jeffrey Choi
(74) *Attorney, Agent, or Firm*—Blynn L. Shideler; Krisanne Shideler; BLK Law Group (57) ABSTRACT

An integrated tail mounted blood pressure monitor and pulse oximeter system includes a tail blood flow occlusion member configured to selectively occlude blood flow through the tail; a sensor coupled to the tail blood flow occlusion member detecting a degree of operation thereof; Light sources coupled to the tail closer to the distal end of the tail than the tail blood flow occlusion member, and selectively directing light of two different wavelengths into the tail; a light receiver coupled to the tail and selectively receiving a signal associated with light directed into the tail from the light sources; and a controller configured to selectively determine blood pressure parameters from the data and pulse oximeter parameters from the data.

12 Claims, 3 Drawing Sheets

U.S. PATENT DOCUMENTS

| | | | |
|---|---|---|---|
| 3,833,864 A | 9/1974 | Kiess et al. | |
| 3,847,483 A | 11/1974 | Shaw et al. | |
| 3,880,006 A | 4/1975 | Poduje | |
| 3,910,701 A | 10/1975 | Henderson et al. | |
| 3,998,550 A | 12/1976 | Konishi et al. | |
| 4,013,067 A | 3/1977 | Kress et al. | |
| 4,059,991 A | 11/1977 | Dybel et al. | |
| 4,086,915 A | 5/1978 | Kofsky et al. | |
| 4,091,803 A | 5/1978 | Pinda | |
| 4,167,331 A | 9/1979 | Nielson | |
| 4,225,410 A | 9/1980 | Pace | |
| 4,266,554 A | 5/1981 | Hamaguri | |
| 4,305,401 A | 12/1981 | Reissmueller et al. | |
| 4,350,165 A | 9/1982 | Striese | |
| 4,362,935 A | 12/1982 | Clark, III | |
| 4,370,984 A | 2/1983 | Cartmell | |
| 4,380,240 A | 4/1983 | Jobsis | |
| 4,406,289 A | 9/1983 | Wesseling et al. | |
| 4,407,272 A | 10/1983 | Yamaguchi | |
| 4,407,290 A | 10/1983 | Wilber | |
| 4,407,298 A | 10/1983 | Lentz et al. | |
| 4,446,715 A | 5/1984 | Bailey | |
| 4,494,550 A | 1/1985 | Blazek et al. | |
| 4,621,643 A | 11/1986 | New et al. | |
| 4,700,708 A | 10/1987 | New, Jr. et al. | |
| 4,830,014 A | 5/1989 | Goodman et al. | |
| 5,490,523 A | 2/1996 | Isaacson et al. | |
| 5,766,127 A * | 6/1998 | Pologe et al. | 600/310 |
| 5,792,052 A | 8/1998 | Isaacson et al. | |
| 5,800,349 A * | 9/1998 | Isaacson et al. | 600/323 |
| 5,927,234 A * | 7/1999 | Siegel | 119/751 |
| 6,436,038 B1 * | 8/2002 | Engstrom | 600/301 |
| 6,446,579 B1 | 9/2002 | Griebling | |
| 6,709,402 B2 * | 3/2004 | Dekker | 600/529 |
| 2005/0065414 A1 * | 3/2005 | Allen et al. | 600/310 |
| 2008/0076989 A1 * | 3/2008 | Hete et al. | 600/323 |

OTHER PUBLICATIONS

Cruz et al., Laboratory Animals, 1998, vol. 32, p. 18-22.
Berkowitz, Investigative ophthalmology & Visual Science, Sep. 1996, vol. 37, No. 10, p. 2089-2098.
Sidwell et al., Antoimocrobial Agents and Chemotherapy, Feb. 1992, p. 473-476.
http://www.kentscientific.com/2002/catalogpagesearch5a.asp-?page-17 Pulse Oximeter for Small Animals.

* cited by examiner

INTEGRATED TAIL MOUNTED BLOOD PRESSURE MONITOR AND PULSE OXIMETER SYSTEM FOR ANIMAL RESEARCH

RELATED APPLICATION

The present application claims the benefit of U.S. Provisional Patent Application Ser. No. 60/978,813, filed Oct. 10, 2007 entitled "Integrated Tail Mounted Blood Pressure Monitor and Pulse Oximeter System for Animal Research"

BACKGROUND INFORMATION

1. Field of the Invention

The present invention relates to an integrated appendage mounted, e.g., tail, pulse oximeter and blood pressure measurement apparatus for animal research.

2. Background Information

Pulse oximetry is a non invasive method that allows for the monitoring of the oxygenation of a subject's blood, generally a human or animal patient or an animal (or possibly human) research subject. The patient/research distinction is particularly important in animals where the data gathering is the primary focus, as opposed to care giving, and where the physiologic data being obtained may, necessarily, be at extreme boundaries for the animal.

As a brief history of pulse oximetry, it has been reported that in 1935 an inventor Matthes developed the first 2-wavelength earlobe $O_2$ saturation meter with red and green filters, later switched to red and infrared filters. This was the first device to measure $O_2$ saturation. Further in 1949 an inventor Wood added a pressure capsule to squeeze blood out of the earlobe to obtain zero setting in an effort to obtain absolute $O_2$ saturation value when blood was readmitted. The concept is similar to today's conventional pulse oximetry but suffered due to unstable photocells and light sources and the method was not used clinically. In 1964 an inventor Shaw assembled the first absolute reading ear oximeter by using eight wavelengths of light which was commercialized by Hewlett Packard, and its use was limited to pulmonary functions due to cost and size.

Effectively, modern pulse oximetry was developed in 1972, by Aoyagi at Nihon Kohden using the ratio of red to infrared light absorption of pulsating components at the measuring site, and this design was commercialized by BIOX/Ohmeda in 1981 and Nellcor, Inc. in 1983. Prior to the introduction of these commercial pulse oximeters, a patient's oxygenation was determined by a painful arterial blood gas, a single point measure which typically took a minimum of 20-30 minutes processing by a laboratory. It is worthy to note that in the absence of oxygenation, damage to the human brain starts in 5 minutes with brain death in a human beginning in another 10-15 minutes. Prior to its introduction, studies in anesthesia journals estimated US patient mortality as a consequence of undetected hypoxemia at 2,000 to 10,000 deaths per year, with no known estimate of patient morbidity. Pulse oximetry has become a standard of care for human patients since the mid to late 1980s. Pulse oximetry has been a critical research tool for obtaining associated physiologic parameters in humans and larger animals for at least as long.

In pulse oximetry a sensor is placed on a thin part of the subject's anatomy, such as a human fingertip or earlobe, or in the case of a neonate, across a foot, and two wavelengths of light, generally red and infrared wavelengths, are passed from one side to the other. Changing absorbance of each of the two wavelengths is measured, allowing determination of the absorbances due to the pulsing arterial alone, excluding venous blood, skin, bone, muscle, fat, etc. Based upon the ratio of changing absorbance of the red and infrared light caused by the difference in color between oxygen-bound (bright red) and oxygen unbound (dark red or blue, in severe cases) blood hemoglobin, a measure of oxygenation (the per cent of hemoglobin molecules bound with oxygen molecules) can be made.

The measured signals are also utilized to determine other physical parameters of the subjects, such as heart rate (pulse rate). Starr Life Sciences, Inc. has utilized pulse oximetry measurements to calculate other physiologic parameters such as breath rate, pulse distension, and breath distention, which can be particularly useful in various research applications.

Regarding human and animal pulse oximetry, the underlying theory of operation remains the same. However, consideration must be made for the particular subject or range of subjects in the design of the pulse oximeter, for example the sensor must fit the desired subject (e.g., a medical pulse oximeter for an adult human finger simply will not adequately fit onto a mouse finger or paw; and regarding signal processing the signal areas that are merely noise in a human application can represent signals of interest in animal applications due to the subject physiology). Consequently there can be significant design considerations in developing a pulse oximeter for small mammals or for neonates or for adult humans, but, again the underlying theory of operation remains substantially the same.

Blood pressure refers to the force exerted by circulating blood on the walls of blood vessels, and constitutes one of the principal vital signs of a patient or subject (human or animal). The pressure of the circulating blood decreases as blood moves through arteries, arterioles, capillaries and veins; the term blood pressure generally refers to arterial blood pressure, i.e., the pressure in the larger arteries, arteries being the blood vessels which take blood away from the heart. Blood pressure in humans is most commonly measured via a device called a sphygmomanometer, which traditionally uses the height of a column of mercury to reflect the circulating pressure. Although many modern blood pressure devices no longer use mercury, blood pressure values are still universally reported in millimeters of mercury.

Systolic pressure is defined as the peak pressure in the arteries, which occurs near the beginning of the cardiac cycle; the diastolic pressure is the lowest pressure (at the resting phase of the cardiac cycle). The average pressure throughout the cardiac cycle is reported as mean arterial pressure; the pulse pressure reflects the difference between the maximum and minimum pressures means.

The ability to accurately and non invasively measure the systolic and diastolic blood pressure, in addition to other blood flow parameters in rodents, and other animals, is of great clinical value to the animal researcher. The general non-invasive blood pressure methodology for measuring blood pressure in rodents comprises utilizing a tail cuff placed proximally on the tail to occlude the blood flow. The subject's tail is threaded through the tail cuff. Upon deflation, one of several types of non invasive blood pressure sensors, placed distal to the occlusion cuff, will attempt to measure the blood pressure. There are several types of non invasive blood pressure sensor technologies: including photoplethysmography, piezoplethysmography, and volume pressure recording. Each of these methods will utilize an occlusion tail-cuff as part of the methodology.

It is worthwhile to note that direct blood pressure measurement in research applications is an invasive surgical procedure with the expense and time involved with invasive procedures, but this invasive procedure is often considered as a more precise measurement and this is used to compare the accuracy of non-invasive blood pressure technologies. Direct blood pressure should be performed on the rodent's carotid artery, rather than the femoral artery.

Photoplethysmography based blood pressure measurements in rodents is the first and oldest sensor type and is a light-based technology, photoplethysmography (PPG) described above in general. The aim is to record the first appearance of the pulse when it re-enters the tail artery during the deflation cycle of the proximal occlusion cuff. Photoplethysmography blood pressure measurement utilizes a standard light source or a LED light source to record the pulse signal wave. As such, this light-based plethysmographic method uses the light source to illuminate a small spot on the tail and attempts to record the pulse.

A second non invasive blood pressure sensor technology is piezoplethysmography. Piezoplethysmography and photoplethysmography both require the same first appearance of pulse in the tail to record the systolic blood pressure and heart rate. Whereas photoplethysmography uses a light source to record the pulse signal, piezoplethysmography utilizes piezoelectric ceramic crystals to record blood pressure readings. From a technical point of view, piezoplethysmography acquires blood pressure readings when the re-appearance of the pulse in the rodent's tail produces a change that can be equated to a voltage shift. The voltage shift momentarily deforms the ceramic crystals and the change is converted to millimeters of mercury for blood pressure readings.

A third sensor technology is volume pressure recording that utilizes a differential pressure transducer to non-invasively measure the blood volume in the tail of a subject.

Representative, commercial rodent tail cuff blood pressure monitoring devices are available from IITC, Life Science, Inc.; Columbus Instruments, Inc.; and Kent Scientific.

Non-invasive tail mounted blood pressure measurement systems for animals should be designed to comfortably warm the animal, reduce the animal's stress and enhance blood flow to the tail. The rodent's core body temperature is very important for accurate and consistent blood pressure measurements. The animal must have adequate blood flow in the tail to acquire a blood pressure signal. Thermo-regulation is the method by which the animal reduces its core body temperature, dissipates heat through its tail and generates tail blood flow. Anesthetized animals may have a lower body temperature than awake animals so additional care must be administered to maintain the animal's proper core body temperature.

An infrared warming blanket or a re-circulating water pump with a warm water blanket are conventional methods to maintain the animal's proper core body temperature. The animal should preferably be warm and comfortable but never hot. Extreme care must be exercised to never overheat the animal. Hot air heating chambers, heat lamps, heating platforms that apply direct heat to the animal's feet have been suggested as well as tail cuff heating devices. However care must be taken with any thermal regulation system to avoid overheating the animal that may increase the animal's respiratory rate, thereby increasing the animal's stress level. These conditions can elicit poor thermo-regulatory responses and may create inconsistent and inaccurate blood pressure readings.

The above discussion notes that blood pressure monitoring in small mammals is somewhat well developed and a very useful tool for researchers. The tail based measurements still provides unique problems for measuring physiologic measurements in rodents. Further, pulse oximetry has been expanded to be effectively applied to small mammals, such as mice as shown in the MouseOx® brand small mammal pulse oximeter available from the assignee, and has provided further useful tools to researchers. There remains a need in the art to effectively expand the useful tools applicable to researchers, to simplify there use and improve the physiologic results.

SUMMARY OF THE INVENTION

One embodiment of the present invention provides an integrated tail mounted blood pressure monitor and pulse oximeter system that includes a tail blood flow occlusion member configured to be secured to a subject's tail and configured to selectively occlude blood flow through the tail; a sensor coupled to the tail blood flow occlusion member configured to detect a degree of operation of the tail blood flow occlusion member; light sources configured to be coupled to the tail in a position closer to the distal end of the tail than the position of the tail blood flow occlusion member, and configured to selectively direct light of at least two different wavelengths into the tail; at least one light receiver configured to be coupled to the tail in a position closer to the distal end of the tail than the position of the tail blood flow occlusion member, and configured to selectively receive a signal associated with light that has been directed into the tail from the light sources; and a controller coupled to the tail blood flow occlusion member for controlling the tail blood flow occlusion member, and coupled to the sensor and the at least one light receiver for receiving data there from, wherein the controller is configured to selectively determine blood pressure parameters from the data and pulse oximeter parameters from the data.

One aspect of the present invention provides a tail mounted blood pressure monitor comprising an animal holder containing an animal; a tail blood flow occlusion member coupled to the holder and configured to be secured to a subject animal's tail and configured to selectively occlude blood flow through the tail, wherein the tail blood flow occlusion member includes two housing halves that are selectively movable toward and away from each other; a sensor coupled to the tail blood flow occlusion member configured to detect a degree of operation of the tail blood flow occlusion member; at least one light source configured to be coupled to the tail in a position closer to the distal end of the tail than the position of the tail blood flow occlusion member, and configured to selectively direct light into the tail; at least one light receiver configured to be coupled to the tail in a position closer to the distal end of the tail than the position of the tail blood flow occlusion member, and configured to selectively receive a signal associated with light that has been directed into the tail from the at least one light source; and a controller coupled to the tail blood flow occlusion member for controlling the tail blood flow occlusion member, and coupled to the sensor and the at least one light receiver for receiving data there from.

One aspect according the present invention provides a tail mounted blood pressure monitor comprising: an animal holder containing an animal; a tail blood flow occlusion member coupled to the holder and configured to be secured to a subject animal's tail and configured to selectively occlude blood flow through the tail, wherein the tail blood flow occlusion member includes an inflatable tail cuff portion that is wrapped around the tail; a sensor coupled to the tail blood flow occlusion member configured to detect a degree of operation of the tail blood flow occlusion member; at least one light source configured to be coupled to the tail in a position closer to the distal end of the tail than the position of the tail blood flow occlusion member, and configured to selectively direct light into the tail; at least one light receiver configured to be coupled to the tail in a position closer to the distal end of the tail than the position of the tail blood flow occlusion member, and configured to selectively receive a signal associated with light that has been directed into the tail from the at least one light source; and a controller coupled to the tail blood flow occlusion member for controlling the tail blood flow occlusion member, and coupled to the sensor and the at least one light receiver for receiving data there from.

One aspect of the present invention provides an integrated blood pressure monitor and pulse oximeter system comprising: a blood flow occlusion member configured to be secured to a subject's appendage and configured to selectively occlude blood flow through the appendage; a sensor coupled to the blood flow occlusion member configured to detect a degree of operation of the blood flow occlusion member; a mounting clip attachable to the appendage in a position closer to the distal end of the appendage than the position of the blood flow occlusion member; light sources carried on the mounting clip and configured to direct light of at least two different wavelengths into the appendage; at least one light receiver carried on the mounting clip and configured to selectively receive a signal associated with light that has been directed into the appendage from the light sources; and a controller coupled to the blood flow occlusion member for controlling the blood flow occlusion member, and coupled to the sensor and the light receivers for receiving data there from, wherein the controller is configured to selectively determine blood pressure parameters from the data and pulse oximeter parameters from the data.

These and other advantages of the present invention will be clarified in the brief description of the preferred embodiment taken together with the drawings in which like reference numerals represent like elements throughout.

DESCRIPTION OF THE PREFFERED EMBODIMENTS

Figure 1:
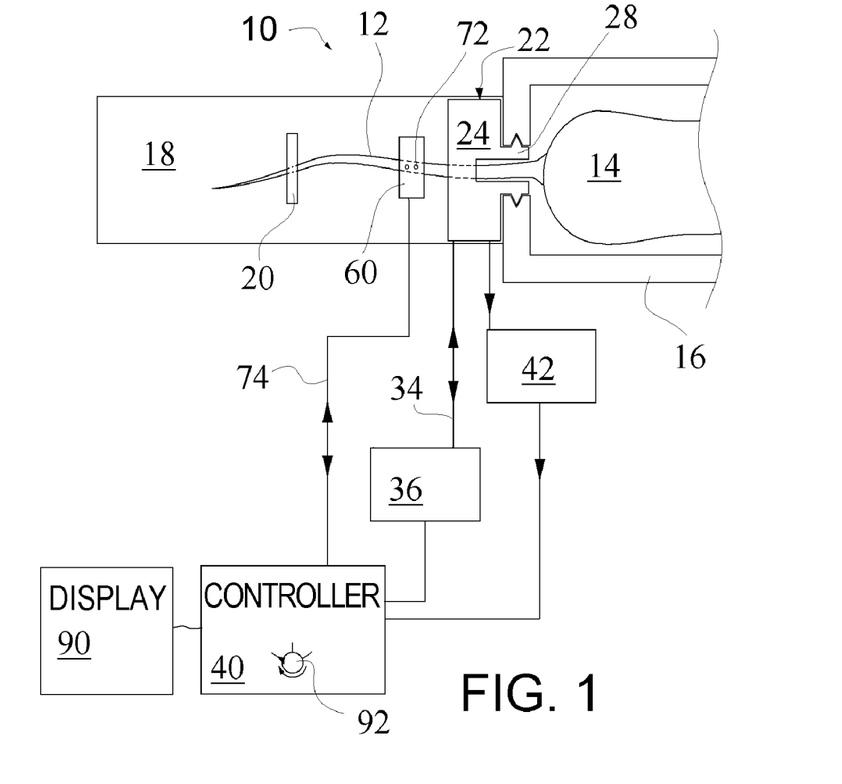
FIG. 1 is a schematic top plan view of an integrated tail mounted blood pressure monitor and pulse oximeter according to one aspect of the present invention.

FIG. 1 is a schematic view of integrated tail mounted blood pressure monitor and pulse oximeter system 10 in accordance with the present invention. The system is designed for the tail 12 of a mouse 14 but can be used with any small mammal.

Figure 4:
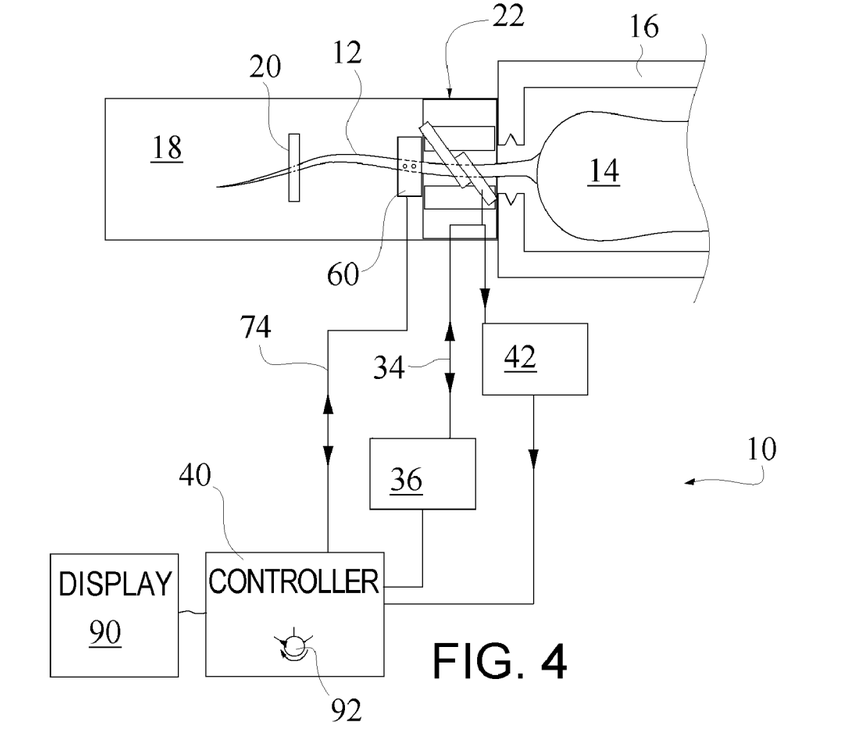
FIG. 4 is a schematic top plan view of an integrated tail mounted blood pressure monitor and pulse oximeter according to one aspect of the present invention.

The mouse 14 is held within an animal holder 16, also known as an animal restraint tube. Animal restraint tubes most often used in research are constructed generally of a clear plastic and have a slit that runs the entire length along the top of the tube. The tube is open on one end, and is closed on the other end (and only the closed end is shown in FIGS. 1 and 4), but the slit described above is joined on the closed end by a slit that runs to the center of the end cap. To use the tube, a researcher grabs the animal's tail 12, and pulls it through the slit from the open end of the tube, toward the closed end. Once the animal, or mouse 14, is pulled all of the way into the tube, a restricting ring or plate is slid into the open end of the tube to allow the user to push the animal, or mouse 12, into the tube and restrict its motion. With the securing of the restricting ring the animal, or mouse 12, is effectively immobilized and the research can proceed. The holder 16 used with the system 10 of the present invention includes a tail support board 18 as part of the holder 12 and the board 18 extends beyond the tail opening and includes slits or the like for one or more tail tie down members 20 that can secure the tail 12 to the support board 18.

Figure 2:
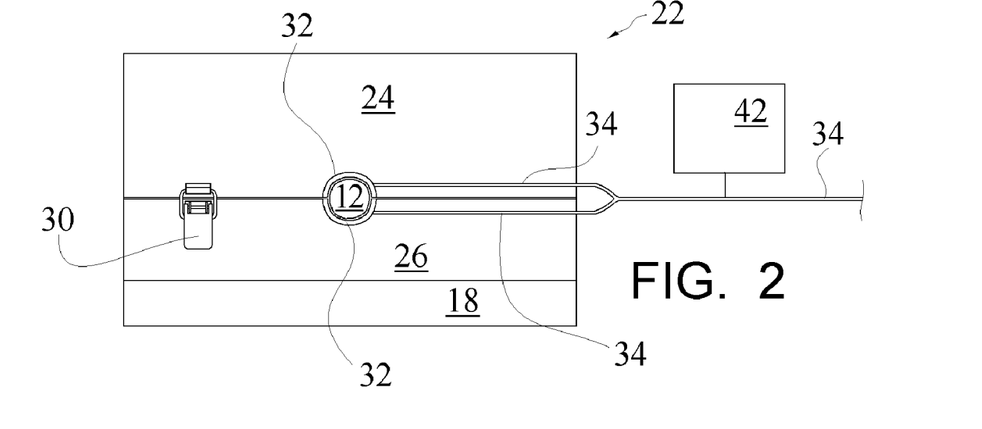
FIG. 2 is a schematic front view of a tail blood flow occlusion member in accordance with one aspect of the present invention.

The system 10 according to the present invention includes a tail blood flow occlusion member 22 configured to be secured to an animal subject's tail 12 and selectively occlude blood flow through the tail 12. FIG. 2 illustrates a first embodiment of the tail blood flow occlusion member 22 using a two housing halves 24 and 26 that are selectively movable toward and away from each other. The lower half 26 can be secured to the tail support board 18 and the upper half 24 can be moveable in a slide 28 that engages rails formed in the holder 16. The weight of the upper half 24 may be such that it is held in a closed position via gravity, or a latch 30 may be used to secure the halves 24 and 26 together in the closed, operative position. With the formation of the tail blood flow occlusion member as two halves the tail 12 need not be "threaded" through a closed opening. Once the tail 12 is properly positioned on the board 18 on top of the lower half 26, the upper half 24 can be slid into position.

The upper and lower halves 24 and 26 include aligned tail receiving recesses as shown. Further each recess includes a respective inflatable tail cuff portion 32. With the tail 12 in the recesses and the upper and lower halves positioned together, the inflatable tail cuff portions substantially encircle the tail 12. Inflation/deflation lines 34 extend to each tail portion 32 for selectively inflating and deflating the tail cuff portions 32 from an actuator 36, such as a pump, controlled via controller 40. A sensor 42 is coupled to the tail cuff portions 32 in a manner to determine the relative pressure within the cuff portions 32 whereby the sensor 42 is configured to detect a degree of operation of the tail blood flow occlusion member 22. The sensor 42 is coupled to the controller 40 to supply data thereto. In addition to conventional operation as a cuff sensor in a blood pressure device, the sensor 42 can be used to indicate when the tail blood flow occlusion member 22 is not in use and the pulse oximetry measurements can be made with the system 10 without significant problems, assuming there is blood flow in the tail or other appendage being measured.

Figure 3:
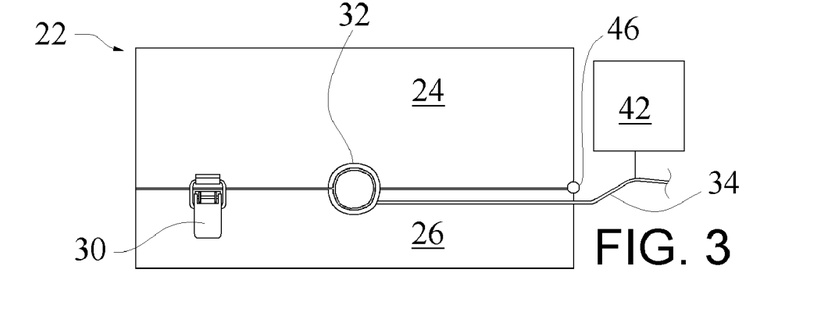
FIG. 3 is a schematic front view of a tail blood flow occlusion member in accordance with another aspect of the present invention.

FIG. 3 illustrates a second embodiment of the tail blood flow occlusion member 22 using a two housing halves 24 and 26 that are selectively movable toward and away from each other. In this embodiment the halves 24 and 26 are pivoted together at pivot 46. A latch 30 may be used to secure the halves 24 and 26 together in the closed, operative position. This embodiment may be easily positioned "vertically" whereby the parting line between the halves is vertical so that it opens upwardly to assist in the tail placement. The attachment of one half 24 or 26 to the board 18 can be made to accommodate the open position of the other half for easy placement of the tail 12. With the formation of the tail blood flow occlusion member as two halves the tail 12 need not be "threaded" through a closed opening. Once the tail 12 is properly positioned within the opened halves 24 and 26, the halves 24 and 26 are closed and latched.

The halves 24 and 26 include aligned tail receiving recesses as shown. Further the recesses include a single inflatable tail cuff portion 32. With the tail 12 in the recesses and the halves 24 and 26 positioned together, the inflatable tail cuff portion 32 substantially encircles the tail 12. An inflation/deflation line 34 extends to the tail portion 32 for selectively inflating and deflating the tail cuff portion 32 from an actuator or pump 36 controlled via controller 40. A sensor 42 is coupled to the tail cuff portion 32 in a manner to determine the relative pressure within the cuff portion 32, whereby the sensor 42 is configured to detect a degree of operation of the tail blood flow occlusion member 22. The sensor 42 is coupled to the controller 40 to supply data thereto. In addition to conventional operation as a cuff sensor in a blood pressure device, the sensor 42 can be used to indicate when the tail blood flow occlusion member 22 is not in use and the pulse oximetry measurements can be efficiently made with the system 10.

Figure 5:
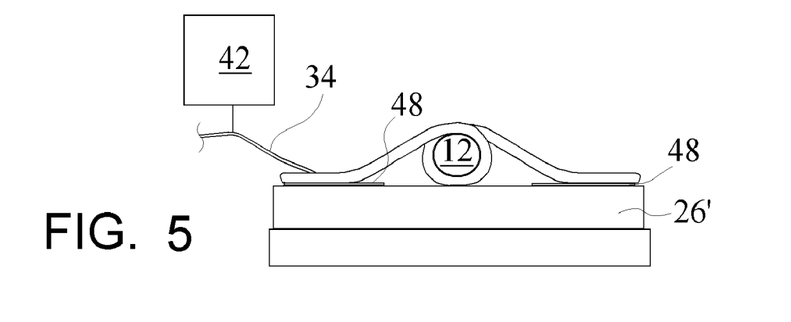
FIG. 5 is a schematic front view of a tail blood flow occlusion member in accordance with another aspect of the present invention.

FIGS. 4 and 5 illustrate a further inflatable cuff 32 version of the blood flow occlusion member 22 in accordance with the present invention. In this embodiment the inflatable cuff 32 is wrapped around the tail 12 and secured at the ends thereof to a base 26' that is secured to the board 18. Releasable fasteners, such as hook and loop type fasteners 48 can be utilized to secure the ends of the cuff 32 to the base 26'. The material forming the cuff 32 can engage with the fastener material 48 or additional material that does engage with the material 48 can be added to the ends of the cuff 32 as needed. Further, the base 26' can be eliminated and the fasteners 48 secured directly to the board 18.

With the formation of the tail blood flow occlusion member 22 with a wrap around tail cuff 32, the tail 12 need not be "threaded" through a closed opening. Once the tail 12 is properly positioned on the un-wrapped (i.e. laid open) cuff 32, the ends of the cuff are wrapped around the tail 12 and secured to the base 26', whereby the inflatable tail cuff portion 32 substantially encircles the tail 12. An inflation/deflation line 34 extends to the tail cuff portion 32 for selectively inflating and deflating the tail cuff portion 32 from an actuator or pump 36 controlled via controller 40. A sensor 42, as in the embodiments described above, is coupled to the tail cuff portion 32 in a manner to determine the relative pressure within the cuff portion 32, whereby the sensor 42 is configured to detect a degree of operation of the tail blood flow occlusion member 22. The sensor 42 is coupled to the controller 40 to supply data thereto. Again, with this embodiment, in addition to conventional operation as a cuff sensor in a blood pressure device, the sensor 42 can be used to indicate when the tail blood flow occlusion member 22 is not in use and the pulse oximetry measurements can be efficiently made with the system 10, assuming there is blood flow in the tail or other appendage of the subject.

Figure 6:
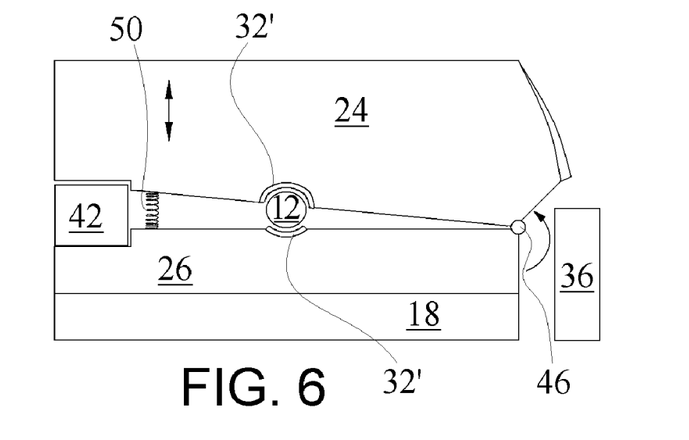
FIG. 6 is a schematic front view of a tail blood flow occlusion member in accordance with another aspect of the present invention.

FIG. 6 illustrates a further embodiment of the tail blood flow occlusion member 22 using a two housing halves 24 and 26 that are selectively movable toward and away from each other, without using an inflatable cuff. In this embodiment the halves 24 and 26 are pivoted together at pivot 46. The halves 24 and 26 include aligned tail receiving recesses with each recess including a tail engaging member 32'. The tail engaging member 32' may be a rubber strip or other resilient member to distribute the force of the closing halves 24 and 26. Unlike earlier versions the recesses in the halves 24 and 26 do not completely accommodate the tail 12 as it is the movement of the halves 24 and 26 together that acts to occlude the blood flow. The recesses could be eliminated completely from the halves 24 and 26, but the presence of some recess portion is believed to assist in tail placement. An actuator 36, such as a linear motor or solenoid, controlled via controller 40 is used to move the halves 24 and 26 in a controlled manner toward and away from each other.

A sensor 42 is coupled to halves 24 and 26 and/or to the actuator 36 in a manner to determine the relative position or force on the tail 12, whereby the sensor 42 is configured to detect a degree of operation of the tail blood flow occlusion member 22. The sensor 42 may be a position sensor or a force sensor. In this embodiment the data from the sensor 42 must be calibrated to equate to an associated pressure on the tail 12 for the blood pressure calculations. However there is believed to be a correlation to the position of the halves 24 and 26, or the force on the sensor 42 and the associated pressure applied to the tail 12. The sensor 42 is coupled to the controller 40 to supply data thereto. In addition to conventional operation as a cuff sensor in a blood pressure device, the sensor 42 can be used to indicate when the tail blood flow occlusion member 22 is not in use and the pulse oximetry measurements can be efficiently made with the system 10. Again, with the formation of the tail blood flow occlusion member 22 as two halves 24 and 26 the tail 12 need not be "threaded" through a closed opening.

Figure 7:
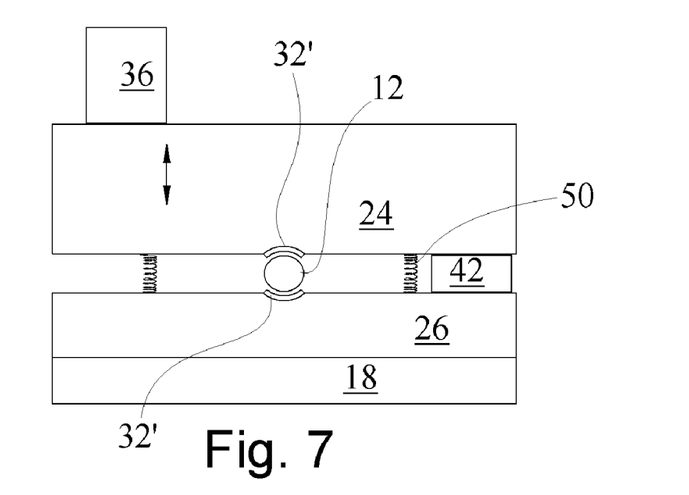
FIG. 7 is a schematic front view of a tail blood flow occlusion member in accordance with another aspect of the present invention.

FIG. 7 illustrates a further embodiment of the tail blood flow occlusion member 22 using a two housing halves 24 and 26 that are selectively movable toward and away from each other, without using an inflatable cuff. The embodiment of FIG. 7 is similar to the embodiment of FIG. 6 in that the halves 24 and 26 do not completely accommodate the tail 12 and it is the movement of the halves 24 and 26 together that acts to occlude the blood flow through the tail 12. The halves 24 and 26 include aligned tail receiving recesses with each recess including a tail engaging member 32'. The tail engaging member 32' may be a rubber strip or other resilient member to distribute the force of the closing halves 24 and 26. Again, the recesses could be eliminated completely from the halves 24 and 26, but the presence of some recess portion is believed to assist in tail placement. An actuator 36, such as a linear motor or solenoid, controlled via controller 40 is used to move the halves 24 and 26 in a controlled manner toward and away from each other. A sensor 42 is coupled to halves 24 and 26 and/or to the actuator 36 in a manner to determine the relative position or force on the tail 12, whereby the sensor 42 is configured to detect a degree of operation of the tail blood flow occlusion member 22. The sensor 42 may be a position sensor or a force sensor. In this embodiment the data from the sensor 42 must be calibrated to equate to an associated pressure on the tail 12 for the blood pressure calculations. The sensor 42 is coupled to the controller 40 to supply data thereto. In addition to conventional operation as a cuff sensor in a blood pressure device, the sensor 42 can be used to indicate when the tail blood flow occlusion member 22 is not in use and the pulse oximetry measurements can be efficiently made with the system 10. Again, with the formation of the tail blood flow occlusion member 22 as two halves 24 and 26 the tail 12 need not be "threaded" through a closed opening. The difference between embodiments 6 and 7 is that the motion of the halves 24 and 26 in FIG. 7 is a linear motion similar to the embodiment of FIGS. 1 and 2.

The embodiments of FIGS. 6 and 7 may further include springs 50 for biasing the halves to an open position that does not place pressure on the tail that could otherwise effect pulse oximetry measurements. Further, with an actuator 36 the sensor 42 may be incorporated into the actuator 36, such as a motor encoder or the like. Further, the actuator could possibly be the addition of given weights, such as pumping water into a receiving reservoir on the upper surface of the upper halve 26, whereby the "sensor" 42 is merely a measurement of the amount of weight that has been added, wherein the weight total will correlate to a specific pressure on the tail. Many alternative embodiments for the blood flow occlusion member 22 are possible within the scope of the present invention and these examples are merely illustrative of some of these possibilities. All of these embodiments provide easy tail placement over earlier tail cuff designs.

Figure 8:
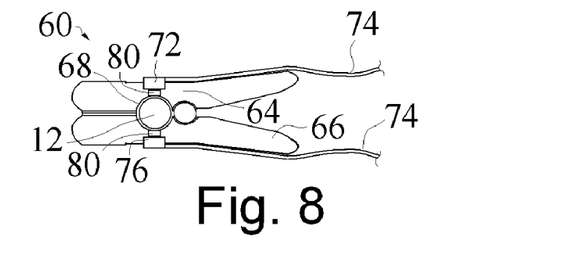
FIG. 8 is a schematic front view of a tail mounting clip with associated light sources and receivers in accordance with one aspect of the present invention.

FIG. 8 illustrates a tail mounting clip 60 for securely mounting physiologic light transmitting and receiving sensors onto the tail 12 in accordance with one embodiment of the present invention. The clip 60 of the present invention provides spring biased halves 64 and 66 pivoted together and biased to a closed position. A transverse circular groove 68 on the tail engaging faces of the halves 64 and 66 is configured to receive and locate the tail 12 therein. The one halve 64 includes a plurality of light sources 72, with leads 74 extending to controller 40. The other halve 66 includes at least one receiver 76, or photo-detectors, configured to receive the light transmitted through the tail 12 from the light sources 72 and coupled to the controller 40 via leads 74. The light sources supply light of at least two distinct wavelengths, generally red and infrared, as is conventional in pulse oximetry. The use of the clips, in general, is known in the pulse oximetry art for coupling associated sensors, such as the LED sources and photo-detectors. The groove 68 makes the clip 60 particularly well suited as a tail mounting element. The groove 68 may be circular in cross section and extends generally perpendicular across the halves 64 and 66 and is preferably sized to accommodate a conventional subject's tail 12 as shown schematically in FIG. 8. The clip 68 may be formed of a non-translucent plastic material and designed to minimize ambient light received by the receivers 76 whereby apertures 80 are supplied to accommodate the desired light transmission and receipt.

In the illustrated but non-limiting embodiment of the present invention the clip 60 is a spring-loaded pivoted body type clamp. The halves 64 and 66 could be attached with some other method, including adhesives, magnetic elements, tape, or combinations thereof without departing from the scope of the present invention. The illustrated embodiment also possesses the rounded, transverse groove 48 on both halves 64 and 66 of the clip 60, but a single tail receiving groove could be provided on only one clip half. Additionally, the groove 48 could have a variable cross-sectional shape, and does not have to be limited to semi-circular. It could also be V-groove, or square in cross-section. The illustrated embodiment uses groove 48 running transverse to the direction of the clip 60, it could also run axially with the clip 60, or at any angle between.

As shown the light sources 72 are configured to be coupled to the tail 12 in a position closer to the distal end of the tail 60 than the position of the tail blood flow occlusion member 22, and configured to selectively direct light of at least two different wavelengths into the tail 12. Further the at least one light receiver 76 is configured to be coupled to the tail 12 in a position closer to the distal end of the tail 12 than the position of the tail blood flow occlusion member 22, and is configured to selectively receive a signal associated with light that has been directed into the tail 12 from the light sources 72.

The controller 40 coupled to the tail blood flow occlusion member 22 for controlling the tail blood flow occlusion member 22, and is coupled to the sensor 42 and the light receivers 76 for receiving data there from.

The key aspect of the present invention is that the controller 40 is configured to selectively determine blood pressure parameters from the data and pulse oximeter parameters from the data. In one operational mode the blood flow occlusion member 22 and clip 60, with controller 40 combine to form a photoplethysmography based blood pressure measurement device. As noted above the aim of such a device is to record the first appearance of the pulse when it re-enters the tail artery during the deflation cycle of the proximal occlusion cuff. Conventional photoplethysmography blood pressure measurement utilizes a standard light source, or a LED light source, to record the pulse signal wave. The signal processing required for such determinations is known to those of ordinary skill in this art, and representative example of such processing is found in the MouseOx® brand small animal pulse oximeters available from the assignee since late 2005 and to the present filing of this application. The results of such calculations can be displayed on an associated display 90. In the blood pressure monitoring mode it is common to have the device cycle through measurements periodically.

In a second operational mode the system 10 obtains pulse oximeter measurements from clip 60. The signal processing of such devices is known from Starr Life Sciences Mouse Ox® brand pulse oximeters, as noted above, and such results can be displayed to the display 90. The sensor 42 can be used in the pulse oximetry mode to assure that the blood flow occlusion member is not obstructing blood flow through the tail 12, which could other-wise detrimentally affect the results of the pulse oximetry measurements. A selector 94 can be provided on the controller to allow the user to select between pulse oximetry measurements with the system 10, blood pressure measurements with the system 10, or both. When selecting both it is expected that the system will cycle through the blood pressure measurements on a given timing cycle (e.g. one blood pressure measurement every 3 minutes) and obtain pulse oximetry measurements during the "off" cycles Although the present invention has been described with particularity herein, the scope of the present invention is not limited to the specific embodiment disclosed. It will be apparent to those of ordinary skill in the art that various modifications may be made to the present invention without departing from the spirit and scope thereof. For example, although particularly well suited for the tail of a subject animal, the present invention can be deployed on other appendages of a subject animal.

What is claimed is:

1. An integrated tail mounted blood pressure monitor and pulse oximeter system comprising:

A tail blood flow occlusion member configured to be secured to a subject's tail and selectively occlude blood flow through the tail;

A sensor coupled to the tail blood flow occlusion member configured to detect a degree of operation of the tail blood flow occlusion member;

Light sources configured to be coupled to the tail in a position closer to the distal end of the tail than the position of the tail blood flow occlusion member, and configured to selectively direct light of at least two different wavelengths into the tail;

At least one Light receiver configured to be coupled to the tail in a position closer to the distal end of the tail than the position of the tail blood flow occlusion member, and configured to selectively receive a signal associated with light that has been directed into the tail from the light sources;

Controller coupled to the tail blood flow occlusion member for controlling the tail blood flow occlusion member, and coupled to the sensor and the at least one light receivers for receiving data there from, wherein the controller is configured to selectively determine blood pressure parameters from the data and pulse oximeter parameters from the data, wherein said pulse oximeter parameters include breath rate, pulse distention, and breath distention.

2. The integrated tail mounted blood pressure monitor and pulse oximeter system according to claim 1 wherein the tail blood flow occlusion member includes at least one inflatable tail cuff portion.

3. The integrated tail mounted blood pressure monitor and pulse oximeter system according to claim 1 wherein the tail blood flow occlusion member includes two housing halves that are selectively movable toward and away from each other.

4. The integrated tail mounted blood pressure monitor and pulse oximeter system according to claim 3 wherein a spring bias holds the two housing halves in a relaxed, non-blood flow occluding position.

5. The integrated tail mounted blood pressure monitor and pulse oximeter system according to claim 3 wherein the movement of the housing halves toward each other is configured to selectively cut off blood flow through the tail.

6. The integrated tail mounted blood pressure monitor and pulse oximeter system according to claim 1 wherein the tail blood flow occlusion member includes an inflatable tail cuff portion that is wrapped around the tail.

7. The integrated tail mounted blood pressure monitor and pulse oximeter system according to claim 1 further including an animal holder for containing the animal and wherein the tail blood flow occlusion member is secured to the holder.

8. An integrated blood pressure monitor and pulse oximeter system comprising:

A blood flow occlusion member configured to be secured to a subject's appendage and selectively occlude blood flow through the appendage;

A sensor coupled to the blood flow occlusion member configured to detect a degree of operation of the blood flow occlusion member;

A mounting clip attachable to the appendage in a position closer to the distal end of the appendage than the position of the blood flow occlusion member;

Light sources carried on the mounting clip and configured to direct light of at least two different wavelengths into the appendage;

At least one Light receiver carried on the mounting clip and configured to selectively receive a signal associated with light that has been directed into the appendage from the light sources;

Controller coupled to the blood flow occlusion member for controlling the blood flow occlusion member, and coupled to the sensor and the at least one light receivers for receiving data there from, wherein the controller is configured to selectively determine blood pressure parameters from the data and pulse oximeter parameters from the data, wherein said pulse oximeter parameters include breath rate, pulse distention, and breath distention.

9. The integrated blood pressure monitor and pulse oximeter system according to claim 8 wherein the blood flow occlusion member includes two housing halves that are selectively movable toward and away from each other.

10. The integrated tail mounted blood pressure monitor and pulse system oximeter according to claim 9 wherein a spring bias holds the two housing halves in a relaxed, non-blood flow occluding position.

11. The integrated blood pressure monitor and pulse oximeter system according to claim 9 wherein the movement of the housing halves toward each other is configured to selectively cut off blood flow through the appendage.

12. The integrated blood pressure monitor and pulse oximeter system according to claim 8 wherein the blood flow occlusion member includes an inflatable cuff portion that is wrapped around the appendage, and further including a subject holder containing the subject and wherein the blood flow occlusion member is secured to the holder.

* * * * *